United States Patent
Reinhard et al.

(10) Patent No.: US 6,624,119 B1
(45) Date of Patent: Sep. 23, 2003

(54) 3-[BENZ(OX/THI)AZOL-7-YL]-1H-PYRIMIDINE-2,4-DIONES

(75) Inventors: Robert Reinhard, Ludwigshafen (DE); Gerhard Hamprecht, Weinheim (DE); Peter Schäfer, Ottersheim (DE); Cyrill Zagar, Ludwigshafen (DE); Martina Otten, Ludwigshafen (DE); Karl-Otto Westphalen, Speyer (DE); Helmut Walter, Obrigheim (DE); Olaf Menke, Altleiningen (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/830,961

(22) PCT Filed: Nov. 6, 1999

(86) PCT No.: PCT/EP99/08514

§ 371 (c)(1),
(2), (4) Date: May 3, 2001

(87) PCT Pub. No.: WO00/28822

PCT Pub. Date: May 25, 2000

(30) Foreign Application Priority Data

Nov. 16, 1998 (DE) .......................... 198 52 802

(51) Int. Cl.[7] .................... C07D 413/04; C07D 417/04; C07D 413/14; A01N 43/78
(52) U.S. Cl. .......................... 504/243; 544/310
(58) Field of Search .................. 544/310; 504/243

(56) References Cited

U.S. PATENT DOCUMENTS

| 4,859,229 A | 8/1989 | Wenger et al. .................. 71/92 |
| 5,169,430 A | 12/1992 | Strunk et al. .................. 71/92 |
| 5,888,940 A | 3/1999 | Heistracher et al. ........ 504/243 |

FOREIGN PATENT DOCUMENTS

| EP | 255 047 | 2/1988 |
| EP | 438 209 | 7/1991 |
| EP | 869 123 | 10/1998 |
| JP | 5-25143 | 2/1993 |
| JP | WO 98/38188 | 9/1998 |
| WO | WO 95/17096 | 6/1995 |
| WO | WO 97/08170 | 3/1997 |
| WO | WO 97/08171 | 3/1997 |
| WO | WO 97/12884 | 4/1997 |
| WO | WO 97/12886 | 4/1997 |
| WO | WO 98/33796 | 8/1998 |
| WO | WO 99/31091 | * 6/1999 |

* cited by examiner

*Primary Examiner*—Deepak Rao
(74) *Attorney, Agent, or Firm*—Keil & Weinkauf

(57) ABSTRACT

The invention relates to herbicidally effective 3-{benz(ox/thi)azol-7-yl}-1H-pyrimidine-2,4-diones of formula (I) wherein X=oxygen or sulphur, Y=oxygen or sulphur; Z=chemical bond, $C_1$–$C_4$-alkylene, O, S, SO, $SO_2$; $R^1$=H, $NH_2$, $C_1$–$C_6$-alkyl, $C_1$–$C_6$-alkyl halide; $R^2$=H, halogen, $C_1$–$C_6$-alkyl, $C_1$–$C_6$-alkyl halide, $C_1$–$C_6$-alkylthio, $C_1$–$C_6$-alkylsulfinyl or $C_1C_6$-alkylsulfonyl; $R^3$=H, halogen, $C_1$–$C_6$-alkyl; $R^4$=H, halogen; $R^5$=CN, halogen, $C_1$–$C_6$-alkyl, $C_1$–$C_6$-alkyl halide, $C_1$–$C_6$-alkoxy or $C_1$–$C_6$-halogenalkoxy; $R^6$=H, $C_3$–$C_7$-cycloalkyl containing a 3 to 7-membered saturated heterocyclyl and one or more oxygen and/or sulphur atoms, whereby each heterocyclic ring may contain a carbonyl or thiocarbonyl ring member. The invention also relates to the agriculturally usable salts of the compounds of formula (I).

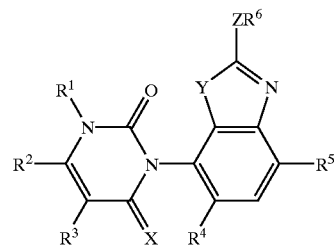

10 Claims, No Drawings

3-[BENZ(OX/THI)AZOL-7-YL]-1H-PYRIMIDINE-2,4-DIONES

This application is a 371 of PCT/EP99/08514 filed Nov. 6, 1999.

The present invention relates to 3-[benz(ox/othi)azol-7-yl]-1H-pyrimidine-2,4-diones of the formula I

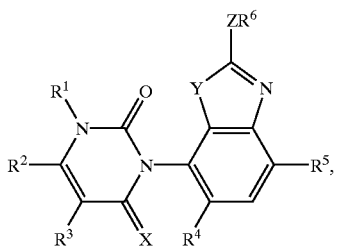

I in which:
- X is oxygen or sulfur;
- Y is oxygen or sulfur;
- Z is a chemical bond, $C_1$–$C_4$-alkylene, oxygen, sulfur, SO or $SO_2$;
- $R^1$ is hydrogen, amino, $C_1$–$C_6$-alkyl or $C_1$–$C_6$-haloalkyl;
- $R^2$ is hydrogen, halogen, $C_1$–$C_6$-alkyl, $C_1$–$C_6$-haloalkyl, $C_1$–$C_6$-alkylthio, $C_1$–$C_6$-alkylsulfinyl or $C_1$–$C_6$-alkylsulfonyl;
- $R^3$ is hydrogen, halogen or $C_1$–$C_6$-alkyl;
- $R^4$ is hydrogen or halogen;
- $R^5$ is cyano, halogen, $C_1$–$C_6$-alkyl, $C_1$–$C_6$-haloalkyl, $C_1$–$C_6$-alkoxy or $C_1$–$C_6$-haloalkoxy;
- $R^6$ is hydrogen, $C_3$–$C_7$-cycloalkyl or 3- to 7-membered saturated heterocyclyl containing one or more oxygen and/or sulfur atoms, where each cycloalkyl and each heterocyclyl ring may contain a carbonyl or thiocarbonyl ring member, and where each cycloalkyl and heterocyclyl ring may be unsubstituted or may carry from one to four substituents, in each case selected from the group consisting of cyano, nitro, amino, hydroxyl, halogen, $C_1$–$C_4$-alkyl, $C_1$–$C_4$-haloalkyl, $C_1$–$C_4$-cyanoalkyl, $C_1$–$C_4$-hydroxyalkyl, $C_1$–$C_4$-aminoalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy, di($C_1$–$C_4$-alkyl)amino, $C_3$–$C_6$-alkenyl, $C_3$–$C_6$-alkynyl, $C_3$–$C_4$-alkenyloxy, $C_3$–$C_4$-alkenylthio, $C_3$–$C_4$-alkynyloxy and $C_3$–$C_4$-alkynylthio, with the proviso that $R^6$ is hydrogen only if Y is oxygen and Z is a chemical bond and that $R^6$ is not $C_3$–$C_6$-cycloalkyl if Y is sulfur, and the agriculturally useful salts of the compounds I.

Moreover, the invention relates to
- the use of the compounds I as herbicides,
- herbicidal compositions comprising the compounds I as active substances,
- processes for preparing the compounds I and herbicidal compositions using the compounds I,
- methods for controlling undesirable vegetation using the compounds I, and
- intermediates of the formulae III, IV, V and VI for preparing the compounds I.

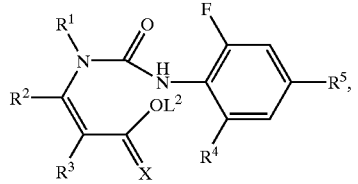

III

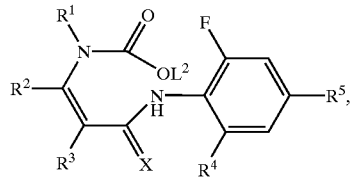

IV

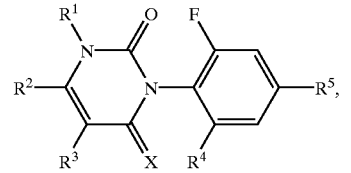

V

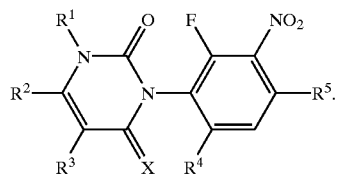

VI

WO 97/08170 describes certain 3-(benz(ox/othi)azol-7-yl)-6-(trifluoromethyl)uracils for use as herbicides. Other 3-(benzothiazol-7-yl)uracils and their use as herbicides and for the desiccation/defoliation of plants are described in WO 97/08171. WO 97/12886 provides, inter alia, certain 3-benzisoxazol-7-yl-2,4-(1H,3H)pyrimidinediones which are said to have herbicidal and desiccant action.

It is an object of the present invention to provide novel herbicidally active uracil compounds which allow better targeted control of undesirable plants than the known uracil compounds.

We have found that this object is achieved by the present 3-[benz(ox/othi)azol-7-yl]-1H-pyrimidine-2,4-diones of the formula I.

We have furthermore found herbicidal compositions comprising the compounds I and having very good herbicidal action. Moreover, we have found processes for preparing these compositions and methods for controlling undesirable vegetation using the compounds I.

Depending on the substitution pattern, compounds of the formula I may contain one or more chiral centers and, if this is the case, are present as enantiomers or mixtures of diastereomers. The invention provides both the pure enantiomers or diastereomers and mixtures thereof.

Suitable agriculturally useful salts are in particular the salts of those cations or the acid addition salts of those acids whose cations or anions, respectively, do not adversely affect the herbicidal activity of the compounds I. Thus, suitable cations are, in particular, ions of the alkali metals, preferably sodium and potassium, of the alkaline earth metals, preferably calcium, magnesium and barium, and of the transition metals, preferably manganese, copper, zinc and iron, and also the ammonium ion which, if desired, may carry from one to four $C_1$–$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of usable acid addition salts are primarily chloride, bromide, fluoride, hydrogen sulfate, sulfate, dihydrogen phosphate, hydrogen phosphate, phosphate, nitrage, hydrogen carbonate, carbonate, hexafluorosilicate, hexafluorophosphate, benzoate, and also the anions of $C_1$–$C_4$-alkanoic acids, preferably formate, acetate, propionate and butyrate. They can be formed by reacting I with an acid of the corresponding anion, preferably hydrochloric acid, hydrobromic acid, sulfuric acid, phosphoric acid or nitric acid.

The organic moieties mentioned in the definition of the substituents $R^1$, $R^2$, $R^3$, $R^5$ and $R^6$ or as radicals on saturated cycloalkyl or saturated heterocyclic rings are—like the term halogen—collective terms for individual enumerations of the individual group members. All hydrocarbon chains, i.e. all alkyl, haloalkyl, cyanoalkyl, hydroxyalkyl, aminoalkyl, alkoxy, haloalkoxy, alkylthio, haloalkylthio, alkylsulfinyl, alkylsulfonyl, haloalkylsulfonyl, alkenyl, alkenyloxy, alkenylthio, alkynyl, alkynyloxy and alkynylthio moieties can be straight-chain or branched. Halogenated substituents preferably carry from one to five identical or different halogen atoms. The meaning of halogen is in each case fluorine, chlorine, bromine or iodine.

Examples of other meanings are:

$C_1$–$C_4$-alkyl: methyl, ethyl, n-propyl, isopropyl, n-butyl, isobutyl, sec-butyl or tert-butyl;

$C_1$–$C_4$-alkylene: methylene, 1,2-ethylene, 1,1-ethylene, 1,3-propylene, 1,2-propylene, 2,2-propylene, 1,4-butylene or 2,3-butylene;

$C_1$–$C_4$-haloalkyl: a $C_1$–$C_4$-alkyl radical as mentioned above which is partially or fully substituted by fluorine, chlorine, bromine and/or iodine, i.e., for example, $CH_2F$, $CHF_2$, $CF_3$, $CH_2Cl$, $CH(Cl)_2$, $C(Cl)_3$, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-alkyl: a $C_1$–$C_4$-alkyl radical as mentioned above or, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $CH_3$, $C_2H_5$, $CH_2$—$C_2H_5$, $CH(CH_3)_2$, n-butyl, $C(CH_3)_3$, n-pentyl or n-hexyl;

$C_1$–$C_6$-haloalkyl: a $C_1$–$C_6$-alkyl radical as mentioned above which is partially or fully substituted by fluorine, chlorine, bromine and/or iodine, i.e., for example, one of the radicals mentioned under $C_1$–$C_4$-haloalkyl or 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl;

cyano-$C_1$–$C_4$-alkyl: $CH_2CN$, 1-cyanoethyl, 2-cyanoethyl, 1-cyanoprop-1-yl, 2-cyanoprop-1-yl, 3-cyanoprop-1-yl, 1-cyanobut-1-yl, 2-cyanobut-1-yl, 3-cyanobut-1-yl, 4-cyanobut-1-yl, 1-cyanobut-2-yl, 2-cyanobut-2-yl, 3-cyanobut-2-yl, 4-cyanobut-2-yl, 1-($CH_2CN$)eth-1-yl, 1-($CH_2CN$)-1-($CH_3$)eth-1-yl or 1-($CH_2CN$)prop-1-yl;

hydroxy-$C_1$–$C_4$-alkyl: $CH_2OH$, 1-hydroxyethyl, 2-hydroxyethyl, 1-hydroxyprop-1-yl, 2-hydroxyprop-1-yl, 3-hydroxyprop-1-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 3-hydroxybut-2-yl, 4-hydroxybut-2-yl, 1-($CH_2OH$)eth-1-yl, 1-($CH_2OH$)-1-($CH_3$)eth-1-yl or 1-($CH_2OH$)prop-1-yl;

amino-$C_1$–$C_4$-alkyl: $CH_2NH_2$, 1-aminoethyl, 2-aminoethyl, 1-aminoprop-1-yl, 2-aminoprop-1-yl, 3-aminoprop-1-yl, 1-amino-but-1-yl, 2-aminobut-1-yl, 3-aminobut-1-yl, 4-aminobut-1-yl, 1-aminobut-2-yl, 2-aminobut-2-yl, 3-aminobut-2-yl, 4-amino-but-2-yl, 1-($CH_2NH_2$)eth-1-yl, 1-($CH_2NH_2$)-1-($CH_3$)eth-1-yl or 1-($CH_2NH_2$)prop-1-yl;

$C_1$–$C_4$-alkoxy: $OCH_3$, $OC_2H_5$, $OCH_2$—$C_2H_5$, $OCH(CH_3)_2$, n-butoxy, $OCH(CH_3)$—$C_2H_5$, $OCH_2$—$CH(CH_3)_2$ or $C(CH_3)_3$, preferably $OCH_3$, $OC_2H_5$ or $OCH(CH_3)_2$;

$C_1$–$C_4$-haloalkoxy: a $C_1$–$C_4$-alkoxy radical as mentioned above which is partially or fully substituted by fluorine, chlorine, bromine and/or iodine, i.e., for example, $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy, preferably $OCHF_2$, $OCF_3$, dichlorofluoromethoxy, chlorodifluoromethoxy or 2,2,2-trifluoroethoxy;

$C_1$–$C_6$-alkoxy: a $C_1$–$C_4$-alkoxy radical as mentioned above or, for example, n-pentoxy, 1-methylbutoxy, 2-methylbutoxy, 3-methylbutoxy, 2,2-dimethylpropoxy, 1-ethylpropoxy, n-hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, preferably $OCH_3$, $OC_2H_5$, $OCH_2$—$C_2H_5$, $OCH(CH_3)_2$, n-butoxy, $OC(CH_3)_3$, n-pentoxy or n-hexoxy;

$C_1$–$C_6$-haloalkoxy: a $C_1$–$C_6$-alkoxy radical as mentioned above which is partially or fully substituted by fluorine, chlorine, bromine and/or iodine, i.e., for example, one of the radicals mentioned under $C_1$–$C_4$-haloalkoxy or 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy;

$C_1$–$C_4$-alkylthio: $SCH_3$, $SC_2H_5$, $SCH_2$—$C_2H_5$, $SCH(CH_3)_2$, n-butylthio, $SCH(CH_3)$—$C_2H_5$, $SCH_2$—$CH(CH_3)_2$ or $SC(CH_3)_3$, preferably $SCH_3$ or $SC_2H_5$;

$C_1$–$C_4$-haloalkylthio: a $C_1$–$C_4$-alkylthio radical as mentioned above which is partially or fully substituted by fluorine, chlorine, bromine and/or iodine, i.e., for example, $SCH_2F$, $SCHF_2$, $SCF_3$, $SCH_2Cl$, $SCH(Cl)_2$, $SC(Cl)_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, $SC_2F_5$, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or $SCF_2$—$CF_2$—$C_2F_5$, preferably $SCHF_2$, $SCF_3$, dichlorofluoromethylthio, chlorodifluoromethylthio or 2,2,2-trifluoroethylthio;

$C_1$–$C_6$-alkylthio: a $C_1$–$C_4$-alkylthio radical as mentioned above or, for example, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, preferably $SCH_3$, $SC_2H_5$, $SCH_2$—$C_2H_5$, $SCH(CH_3)_2$, n-butylthio, $SC(CH_3)_3$, n-pentylthio or n-hexylthio;

($C_1$–$C_4$-alkyl)carbonyl: $CO$—$CH_3$, $CO$—$C_2H_5$, $CO$—$CH_2$—$C_2H_5$, $CO$—$CH(CH_3)_2$, n-butylcarbonyl, $CO$—$CH(CH_3)$—$C_2H_5$, $CO$—$CH_2$—$CH(CH_3)_2$ or $CO$—$C(CH_3)_3$, preferably $CO$—$CH_3$ or $CO$—$C_2H_5$;

($C_1$–$C_4$-haloalkyl)carbonyl: a ($C_1$–$C_4$-alkyl)carbonyl radical as mentioned above which is partially or fully substituted by fluorine, chlorine, bromine and/or iodine, i.e., for example, $CO$—$CH_2F$, $CO$—$CHF_2$, $CO$—$CF_3$, $CO$—$CH_2Cl$, $CO$—$CH(Cl)_2$, $CO$—$C(Cl)_3$, chlorofluoromethylcarbonyl, dichlorofluoromethylcarbonyl, chlorodifluoromethylcarbonyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, $CO$—$C_2F_5$, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, $CO$—$CH_2$—$C_2F_5$, $CO$—$CF_2$—$C_2F_5$, 1-($CH_2F$)-2-fluoroethylcarbonyl, 1-($CH_2Cl$)-2-chloroethylcarbonyl, 1-($CH_2Br$)-2-bromoethylcarbonyl, 4-fluorobutylcarbonyl, 4-chlorobutylcarbonyl, 4-bromobutylcarbonyl or $CO$-(n-$C_4F_9$), preferably $CO$—$CF_3$, $CO$—$CH_2Cl$ or 2,2,2-trifluoroethylcarbonyl;

($C_1$–$C_4$-alkyl)carbonyloxy: $O$—$CO$—$CH_3$, $O$—$CO$—$C_2H_5$, $O$—$CO$—$CH_2$—$C_2H_5$, $O$—$CO$—$CH(CH_3)_2$, $O$—$CO$—$CH_2$—$CH_2$—$C_2H_5$, $O$—$CO$—$CH(CH_3)$—$C_2H_5$, $O$—$CO$—$CH_2$—$CH(CH_3)_2$ or $O$—$CO$—$C(CH_3)_3$, preferably $O$—$CO$—$CH_3$ or $O$—$CO$—$C_2H_5$;

($C_1$–$C_4$-haloalkyl)carbonyloxy: a ($C_1$–$C_4$-alkyl)carbonyl radical as mentioned above which is partially or fully substituted by fluorine, chlorine, bromine and/or iodine, i.e., for example, $O$—$CO$—$CH_2F$, $O$—$CO$—$CHF_2$, $O$—$CO$—$CF_3$, $O$—$CO$—$CH_2Cl$, $O$—$CO$—$CH(Cl)_2$, $O$—$CO$—$C(Cl)_3$, chlorofluoromethylcarbonyloxy, dichlorofluoromethylcarbonyloxy, chlorodifluoromethylcarbonyloxy, 2-fluoroethylcarbonyloxy, 2-chloroethylcarbonyloxy, 2-bromoethylcarbonyloxy, 2-iodoethylcarbonyloxy, 2,2-difluoroethylcarbonyloxy, 2,2,2-trifluoroethylcarbonyloxy, 2-chloro-2-fluoroethylcarbonyloxy, 2-chloro-2,2-difluoroethylcarbonyloxy, 2,2-dichloro-2-fluoroethylcarbonyloxy, 2,2,2-trichloroethylcarbonyloxy, $O$—$CO$—$C_2F_5$, 2-fluoropropylcarbonyloxy, 3-fluoropropylcarbonyloxy, 2,2-difluoropropylcarbonyloxy, 2,3-difluoropropylcarbonyloxy, 2-chloropropylcarbonyloxy, 3-chloropropylcarbonyloxy, 2,3-dichloropropylcarbonyloxy, 2-bromopropylcarbonyloxy, 3-bromopropylcarbonyloxy, 3,3,3-trifluoropropylcarbonyloxy, 3,3,3-trichloropropylcarbonyloxy, $O$—$CO$—$CH_2$—$C_2F_5$, $O$—$CO$—$CF_2$—$C_2F_5$, 1-($CH_2F$)-2-fluoroethylcarbonyloxy, 1-($CH_2Cl$)-2-chloroethylcarbonyloxy, 1-($CH_2Br$)-2-bromoethylcarbonyloxy, 4-fluorobutylcarbonyloxy, 4-chlorobutylcarbonyloxy, 4-bromobutylcarbonyloxy or nonafluorobutylcarbonyloxy, preferably $O$—$CO$—$CF_3$, $O$—$CO$—$CH_2Cl$ or 2,2,2-trifluoroethylcarbonyloxy;

($C_1$–$C_4$-alkoxy)carbonyl: $CO$—$OCH_3$, $CO$—$OC_2H_5$, $CO$—$OCH_2$—$C_2H_5$, $CO$—$OCH(CH_3)_2$, n-butoxycarbonyl, $CO$—$OCH(CH_3)$—$C_2H_5$, $CO$—$OCH_2$—$CH(CH_3)_2$ or $CO$—$OC(CH_3)_3$, preferably $CO$—$OCH_3$ or $CO$—$OC_2H_5$;

$C_1$–$C_4$-alkylsulfinyl: $SO$—$CH_3$, $SO$—$C_2H_5$, $SO$—$CH_2$—$C_2H_5$, $SO$—$CH(CH_3)_2$, $SO$-(n-$C_4H_9$), $SO$—$CH(CH_3)$—$C_2H_5$, $SO$—$CH_2$—$CH(CH_3)_2$ or $SO$—$C(CH_3)_3$;

$C_1$–$C_6$-alkylsulfinyl: a $C_1$–$C_4$-alkylsulfinyl radical as mentioned above or $SO$-(n-$C_5H_{11}$), 1-methylbutyl-$SO$, 2-methylbutyl-SO, 3-methylbutyl-SO, 2,2-dimethylpropyl-SO, 1-ethylpropyl-SO, n-hexyl-SO, 1,1-dimethylpropyl-SO, 1,2-dimethylpropyl-SO, 1-methylpentyl-SO, 2-methylpentyl-SO, 3-methylpentyl-SO, 4-methylpentyl-SO, 1,1-dimethylbutyl-SO, 1,2-dimethylbutyl-So, 1,3-dimethylbutyl-SO, 2,2-dimethylbutyl-SO, 2,3-dimethylbutyl-SO, 3,3-dimethylbutyl-SO, 1-ethylbutyl-SO, 2-ethylbutyl-SO, 1,1,2-trimethylpropyl-SO, 1,2,2-trimethylpropyl-SO, 1-ethyl-1-methylpropyl-So or 1-ethyl-2-methylpropyl-SO, preferably SO—CH$_3$, SO—C$_2$H$_5$, SO—CH$_2$—C$_2$H$_5$, SO—CH(CH$_3$)$_2$, SO-(n-C$_4$H$_9$), SO—C(CH$_3$)$_3$, SO-(n-C$_5$H$_{11}$) or SO-(n-C$_6$H$_{13}$);

$C_1$–$C_4$-alkylsulfonyl: SO$_2$—CH$_3$, SO$_2$—C$_2$H$_5$, SO$_2$—CH$_2$—C$_2$H$_5$, SO$_2$—CH(CH$_3$)$_2$, SO$_2$-(n-C$_4$H$_9$), SO$_2$—CH(CH$_3$)—C$_2$H$_5$, SO$_2$—CH$_2$—CH(CH$_2$)$_2$ or SO$_2$—C(CH$_3$)$_3$;

$C_1$–$C_6$-alkylsulfonyl: a $C_1$–$C_4$-alkylsulfonyl radical as mentioned above, or SO$_2$-(n-C$_5$H$_{11}$), 1-methylbutyl-SO$_2$, 2-methylbutyl-SO$_2$, 3-methylbutyl-SO$_2$, 2,2-dimethylpropyl-SO$_2$, 1-ethylpropyl-SO$_2$, n-hexyl-SO$_2$, 1,1-dimethylpropyl-SO$_2$, 1,2-dimethylpropyl-SO$_2$, 1-methylpentyl-SO$_2$, 2-methylpentyl-SO$_2$, 3-methylpentyl-SO$_2$, 4-methylpentyl-SO$_2$, 1,1-dimethylbutyl-SO$_2$, 1,2-dimethylbutyl-SO$_2$, 1,3-dimethylbutyl-SO$_2$, 2,2-dimethylbutyl-SO$_2$, 2,3-dimethylbutyl-SO$_2$, 3,3-dimethylbutyl-SO$_2$, 1-ethylbutyl-SO$_2$, 2-ethylbutyl-SO$_2$, 1,1,2-trimethylpropyl-SO$_2$, 1,2,2-trimethylpropyl-SO$_2$, 1-ethyl-1-methylpropyl-SO$_2$ or 1-ethyl-2-methylpropyl-SO$_2$, preferably SO$_2$—CH$_3$, SO$_2$—C$_2$H$_5$, SO$_2$—CH$_2$—C$_2$H$_5$, SO$_2$—CH(CH$_3$)$_2$, SO$_2$-(n-C$_4$H$_9$), SO$_2$—C(CH$_3$)$_3$, SO$_2$-(n-C$_5$H$_{11}$) or SO$_2$-(n-C$_6$H$_{13}$);

$C_1$–$C_4$-haloalkylsulfonyl: a $C_1$–$C_4$-alkylsulfonyl radical as mentioned above which is partially or fully substituted by fluorine, chlorine, bromine and/or iodine, i.e., for example, SO$_2$—CH$_2$F, SO$_2$—CHF$_2$, SO$_2$—CF$_3$, SO$_2$—CH$_2$Cl, SO$_2$—CH(Cl)$_2$, SO$_2$—C(Cl)$_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, SO$_2$—C$_2$F$_5$, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, SO$_2$—CH$_2$—C$_2$F$_5$, SO$_2$—CF$_2$—C$_2$F$_5$, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl, preferably SO$_2$—CH$_2$Cl, SO$_2$—CF$_3$ or 2,2,2-trifluoroethylsulfonyl;

di($C_1$–$C_4$-alkyl)amino: N(CH$_3$)$_2$, N(C$_2$H$_5$)$_2$, N(CH$_2$—C$_2$H$_5$)$_2$, N[CH(CH$_3$)$_2$]$_2$, N,N-dibutylamino, N,N-di(1-methylpropyl)amino, N,N-di(2-methylpropyl)amino, N[C(CH$_3$)$_3$]$_2$, N-ethyl-N-methylamino, N-methyl-N-propylamino, N[C(CH$_3$)$_3$ ]$_2$, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, preferably N(CH$_3$)$_2$ or N(C$_2$H$_5$)$_2$;

$C_3$–$C_6$-alkenyl: prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_3$–$C_6$-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably prop-2-yn-1-yl;

$C_3$–$C_4$-alkenyloxy: allyloxy, but-1-en-3-yloxy, but-1-en-4-yloxy, but-2-en-1-yloxy, 1-methylprop-2-enyloxy or 2-methylprop-2-enyloxy, preferably allyloxy, $C_3$–$C_4$-alkynyloxy: propargyloxy, but-1-yn-3-yloxy, but-1-yn-4-yloxy, but-2-yn-1-yloxy, 1-methylprop-2-ynyloxy or 2-methylprop-2-ynyloxy, preferably propargyloxy, $C_3$–$C_4$-alkynylthio: propargylthio, but-1-yn-3-ylthio, but-1-yn-4-ylthio, but-2-yn-1-ylthio, 1-methylprop-2-ynylthio or 2-methylprop-2-ynylthio, preferably propargylthio, $C_3$–$C_4$-alkenylthio: allylthio, but-1-en-3-ylthio, but-1-en-4-ylthio, but-2-en-1-ylthio, 1-methylprop-2-enylthio or 2-methylprop-2-enylthio, preferably allylthio, $C_3$–$C_7$-cycloalkyl: cyclopropyl, cyclobutyl, cyclopentyl, cyclohexyl or cycloheptyl, preferably cyclopropyl.

3- to 7-membered saturated heterocyclyl systems are in particular 5 those having
one or two oxygen and/or
one or two sulfur atoms.

The following are examples of saturated hetercycles which may contain a carbonyl or thiocarbonyl ring member:
oxiranyl, thiiranyl, oxetan-2-yl, oxetan-3-yl, thietan-2-yl, thietan-3-yl, tetrahydrofuran-2-yl, tetrahydrofuran-3-yl, tetrahydrothiophen-2-yl, tetrahydrothiophen-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-4-yl, 1,3-dithiepan-5-yl, 1,3-dithiepan-6-yl, 1,4-dioxepan-2-yl and 1,4-dioxepan-7-yl.

All cycloalkyl and heterocyclyl rings are preferably unsubstituted or carry one substituent.

In view of the use of the 3-[benz(ox/othi)azol-7-yl]-1H-pyrimidine-2,4-diones I according to the invention as herbicides, preference is given to those compounds I where the variables are as defined below, in each case on their own or in combination:

X is oxygen;

Y is oxygen;

Z is a chemical bond, $C_1$–$C_4$-alkylene, oxygen or sulfur;

$R^1$ is hydrogen, amino or $C_1$–$C_6$-alkyl;

$R^2$ is hydrogen, halogen, $C_1$–$C_6$-alkyl, $C_1$–$C_6$-haloalkyl or $C_1$–$C_6$-alkylsulfonyl;

$R^3$ is hydrogen;

$R^4$ is hydrogen, fluorine or chlorine;

$R^5$ is cyano or halogen;

$R^6$ is hydrogen, $C_3$–$C_6$-cycloalkyl or 3- to 7-membered saturated heterocyclyl containing an oxygen or sulfur atom, where each cycloalkyl and each heterocyclyl ring may contain a carbonyl or thiocarbonyl ring member, and where each cycloalkyl and heterocyclyl ring may be unsubstituted or may carry from one to four substituents, in each case selected from the group consisting of cyano, nitro, amino, hydroxyl, halogen, $C_1$–$C_4$-alkyl, $C_1$–$C_4$-haloalkyl, $C_1$–$C_4$-cyanoalkyl, $C_1$–$C_4$-hydroxyalkyl, $C_1$–$C_4$-aminoalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy, di($C_1$–$C_4$-alkyl)amino, $C_3$–$C_6$-alkenyl, $C_3$–$C_6$-alkynyl, $C_3$–$C_4$-alkenyloxy, $C_3$–$C_4$-alkenylthio, $C_3$–$C_4$-alkynyloxy and $C_3$–$C_4$-alkynylthio, $R^6$ is in particular hydrogen, $C_3$–$C_6$-cycloalkyl or 3- to 7-membered saturated heterocyclyl containing an oxygen or sulfur atom, where each cycloalkyl and each heterocyclyl ring may contain a carbonyl or thiocarbonyl ring member.

Very particular preference is given to the 3-[benz(ox/othi)azol-7-yl]-1H-pyrimidine-2,4-diones of the formula Ia {=I where X and Y=oxygen, $R^1$=methyl, $R^2$=rifluoromethyl, $R^3$=hydrogen, $R^4$=fluorine, $R^5$=chlorine and Z=a chemical bond}

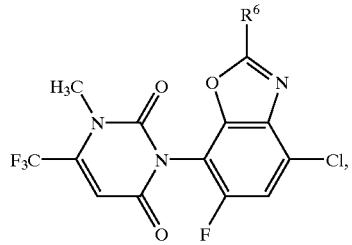

Ia in particular the compounds Ia.1 to Ia. 51 listed in Table 1 below:

TABLE 1

| No. | $R^6$ |
|---|---|
| 1a.1 | cyclopropyl |
| 1a.2 | cyclobutyl |
| 1a.3 | cyclopentyl |
| 1a.4 | cyclohexyl |
| 1a.5 | cycloheptyl |
| 1a.6 | oxiran-2-yl |
| 1a.7 | oxetan-2-yl |
| 1a.8 | tetrahydrofuran-2-yl |
| 1a.9 | tetrahydropyran-2-yl |
| 1a.10 | oxepan-2-yl |
| 1a.11 | thiiran-2-yl |
| 1a.12 | thietan-2-yl |
| 1a.13 | tetrahydrothiofuran-2-yl |
| 1a.14 | tetrahydrothiopyran-2-yl |
| 1a.15 | thiepan-2-yl |
| 1a.16 | oxetan-3-yl |
| 1a.17 | tetrahydrofuran-3-yl |
| 1a.18 | tetrahydropyran-3-yl |
| 1a.19 | oxepan-3-yl |
| 1a.20 | thietan-3-yl |
| 1a.21 | tetrahydrothiofuran-3-yl |
| 1a.22 | tetrahydrothiopyran-3-yl |
| 1a.23 | thiepan-3-yl- |
| 1a.24 | tetrahydropyran-4-yl |
| 1a.25 | oxepan-4-yl |
| 1a.26 | tetrahydrothiopyran-4-yl |
| 1a.27 | thiepan-4-yl |
| 1a.28 | 2-oxocyclopropyl |
| 1a.29 | 2-oxocyclobutyl |
| 1a.30 | 2-oxocyclopentyl |
| 1a.31 | 2-oxocyclohexyl |
| 1a.32 | 2-oxocycloheptyl |
| 1a.33 | 2-thioxocyclopropyl |
| 1a.34 | 2-thioxocyclobutyl |
| 1a.35 | 2-oxooxetan-3-yl |
| 1a.36 | 2-oxotetrahydrofuran-3-yl |

TABLE 1-continued

| No. | R⁶ |
|---|---|
| 1a.37 | 2-Oxo-tetrahydropyran-3-yl |
| 1a.38 | 2-oxooxepan-3-yl |
| 1a.39 | 2-thioxothietan-3-yl |
| 1a.40 | 2-thioxotetrahydrothien-3-yl |
| 1a.41 | 2-thioxotetrahydrothiopyran-3-yl |
| 1a.42 | 2-thioxothiepan-3-yl |
| 1a.43 | 2-thioxooxetan-3-yl |
| 1a.44 | 2-thioxotetrahydrofuran-3-yl |
| 1a.45 | 2-thioxotetrahydropyran-3-yl |
| 1a.46 | 2-thioxooxepan-3-yl |
| 1a.47 | 2-oxothietan-3-yl |
| 1a.48 | 2-oxotetrahydrothien-3-yl |
| 1a.49 | 2-oxotetrahydrothiopyran-3-yl |
| 1a.50 | 2-oxothiepan-3-yl |
| 1a.51 | H |

Furthermore, particular preference is given to the 3-[benz(ox/othi)azol-7-yl]-1H-pyrimidine-2,4-diones of the formulae Ib to Ip, in particular the compounds Ib.1–Ib.51 which differ from the corresponding compounds Ia.1–Ia.51 only in that $R^1$ is hydrogen:

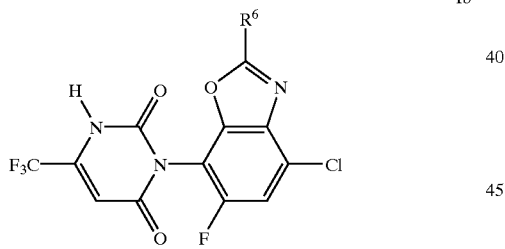

Ib the compounds Ic.5–Ic.50 which differ from the corresponding compounds Ia.5–Ia.50 only in that Y is sulfur:

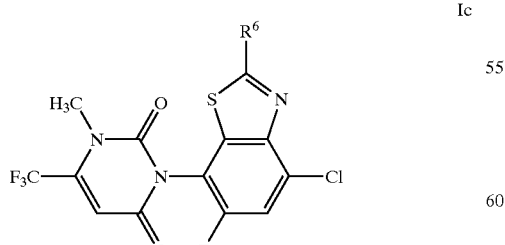

Ic the compounds Id.5–Id.50 which differ from the corresponding compounds Ia.5–Ia.50 only in that $R^1$ is hydrogen and Y is sulfur:

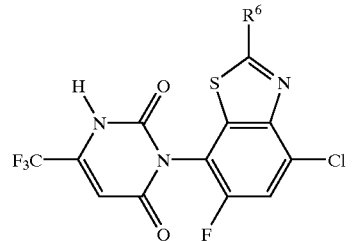

Id the compounds Ie.1–Ie.51 which differ from the corresponding compounds Ia.1–Ia.51 only in that Z is $CH_2$:

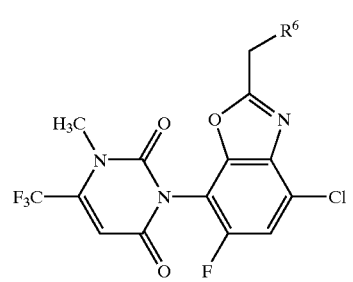

Ie the compounds If.1–If.51 which differ from the corresponding compounds Ia.1–Ia.51 only in that $R^1$ is hydrogen and Z is $CH_2$:

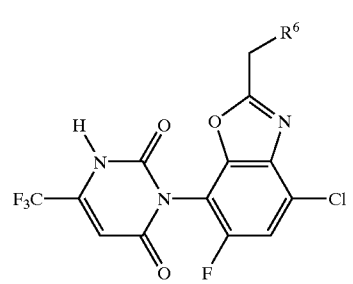

If the compounds Ig.5–Ig.50 which differ from the corresponding compounds Ia.5–Ia.50 only in that Y is sulfur and Z is $CH_2$:

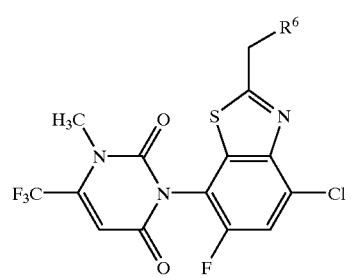

Ig the compounds Ih.5–Ih.50 which differ from the corresponding compounds Ia.5–Ia.50 only in that $R^1$ is hydrogen, Y is sulfur and Z is $CH_2$:

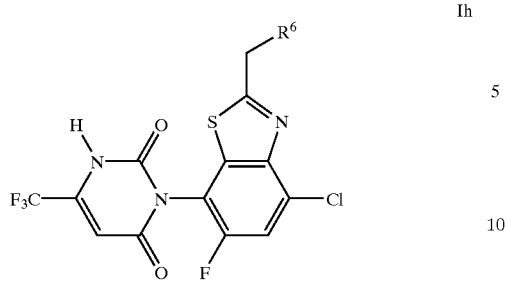

Ih the compounds Ii.1–Ii.51 which differ from the corresponding compounds Ia.1–Ia.51 only in that Z is oxygen:

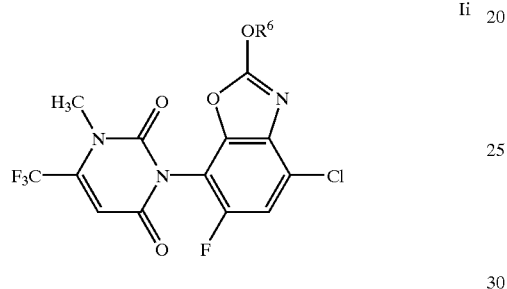

Ii the compounds Ij.1–Ij.51 which differ from the corresponding compounds Ia.1–Ia.51 only in that $R^1$ is hydrogen and Z is oxygen:

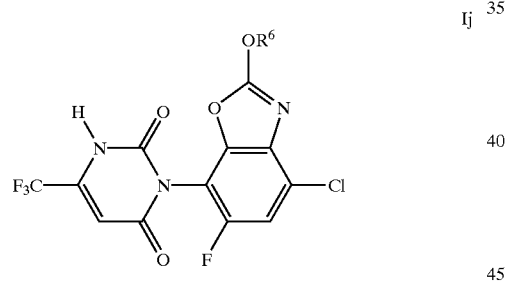

Ij the compounds Ik.5–Ik.50 which differ from the corresponding compounds Ia.5–Ia.50 only in that Y is sulfur and Z is oxygen:

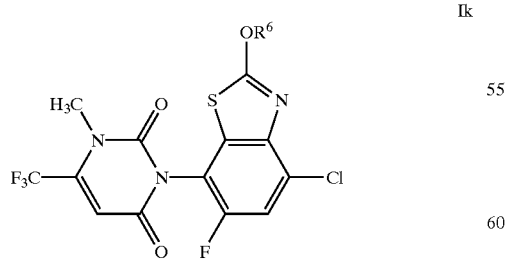

Ik the compounds Il.5–Il.50 which differ from the corresponding compounds Ia.5–Ia.50 only in that $R^1$ is hydrogen, Y is sulfur and Z is oxygen:

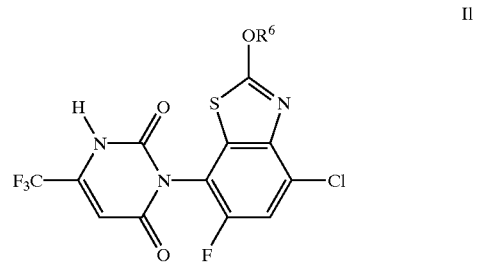

Il the compounds Im.1–Im.51 which differ from the corresponding compounds Ia.1–Ia.51 only in that Z is sulfur:

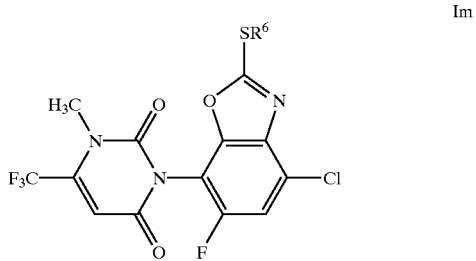

Im the compounds In.1–In.51 which differ from the corresponding compounds Ia.1–Ia.51 only in that $R^1$ is hydrogen and Z is sulfur:

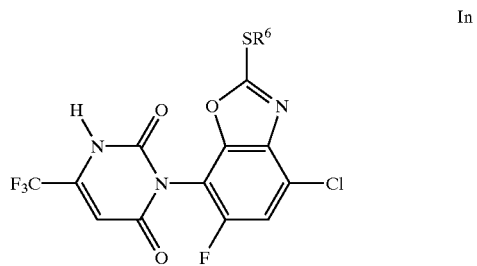

In the compounds Io.5–Io.50 which differ from the corresponding compounds Ia.5–Ia.50 only in that Y and Z are each sulfur:

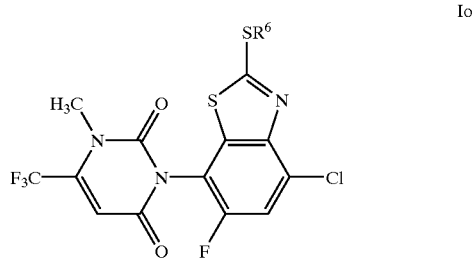

Io the compounds Ip.5–Ip.50 which differ from the corresponding compounds Ia.5–Ia.50 only in that $R^1$ is hydrogen and Y and Z are each sulfur:

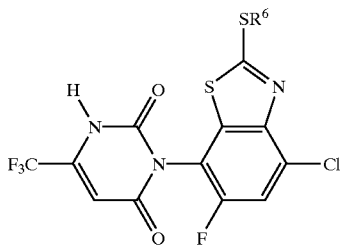

The 3-[benz(ox/othi)azol-7-yl]-1H-pyrimidine-2,4-diones of the formula I according to the invention can be obtained by various routes, for example by one of the processes below:

Process A)
Condensation of a substituted 2-aminophenol or 2-aminothiophenol ith carbonic acid derivatives or carboxylic acid derivatives:

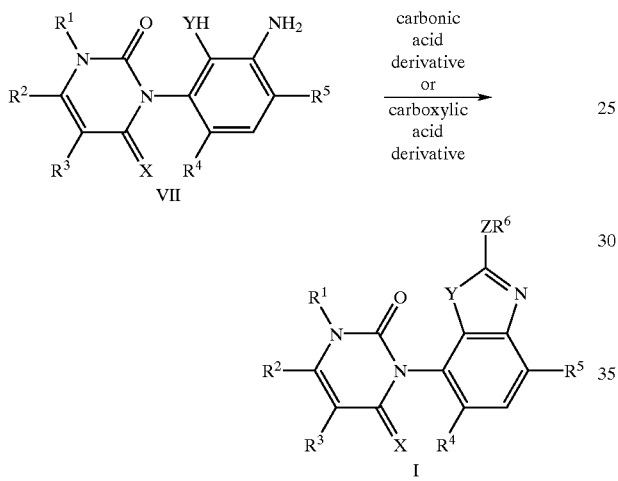

The condensation of bifunctional benzenes VII with carbonic acid derivatives or carboxylic acid derivatives can be carried out in a manner known per se (cf., for example, Houben-Weyl, Methoden der organischen Chemie, Georg Thieme Verlag, Stuttgart, Vol. E8c, 1st edition 1994, pp. 247–284; Vol. E8b, 1st edition 1994, pp. 881–901; Vol. E8a, 1st edition 1993, pp. 1032–1078). Preferred carbonic acid derivatives or carboxylic acid derivatives are the corresponding esters, anhydrides, acyl chlorides, orthoesters, diimides, nitriles, imidoesters, trichloromethyl-substituted compounds, isocyanates and their thio analogs.

Suitable solvents/diluents are, in particular, organic solvents, for example aromatic hydrocarbons, such as benzene, toluene and o-, m-, p-xylene, halogenated hydrocarbons, such as methylene chloride, chloroform and dichloroethane, lower alcohols, such as methanol and ethanol, aliphatic or cyclic ethers, such as dimethoxyethane, tetrahydrofuran and dioxane, carboxylic esters, such as ethyl acetate, or aprotic polar solvents, such as dimethylformamide and dimethyl sulfoxide.

If desired, the reaction can be accelerated by addition of catalytic amounts of an acid. Suitable acids are, in particular, mineral acids, such as hydrochloric acids, or sulfonic acids, such as p-toluenesulfonic acid, or their salts with nitrogen bases, such as pyridine. The amount of acid is preferably at from 0.01 to 5 mol percent, based on the amount of VII.

The reaction temperatures are preferably at from 20° C. to the reflux temperature of the reaction mixture in question, in particular at from 60° C. to reflux temperature.

The carbonic acid derivative or carboxylic acid derivative is employed either in an approximately stoichiometric amount, or in excess. In suitable cases, it is also possible to employ a very large excess, or to carry out the reaction without solvent. Preference is given to approximately stoichiometric amounts or to an excess of up to 10 molar equivalents, based on the amount of VII.

The substituted 2-aminophenols und -thiophenols are expediently obtained by reducing the corresponding 2-nitrophenols or -thiophenols VIII (cf., for example, Houben-weyl, Methoden der organischen Chemie, Georg Thieme Verlag, Stuttgart, Vol. XI/1, 4th edition 1957, p. 431 ff.):

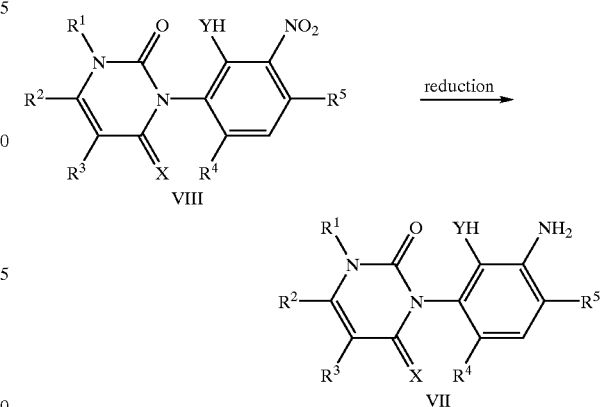

Suitable reducing agents are, in particular elemental metals, such as iron, tin and zinc, hydrogen in the presence of suitable catalyts, such as palladium or platinum on carbon or Raney nickel, or complex hydrides, such as $LiAlH_4$ and $NaBH_4$, if appropriate in the presence of catalysts.

Suitable solvents are usually—depending on the reducing agent—carboxylic acids, such as acetic acid and propionic acid, mineral acids, such as hydrochloric acid or sulfuric acid, alcohols, such as methanol and ethanol, ethers, such as diethyl ether, methyl tert-butyl ether, tetrahydrofuran and dioxane, aromatics, such as benzene and toluene, as well as mixtures of these.

The reactions can be carried out at temperatures of from (−100)° C. to the boiling point of the reaction mixture in question.

The starting materials are usually employed in approximately stoichiometric amounts; however, in individual cases it may be advantageous to employ a multiple excess of one or the other component.

The 2-nitrophenols or -thiophenols VIII can be obtained by reacting precursors IX having various groups attached at the phenol oxygen or at the thiophenol sulfur atom. These can be, for example, alkyl, benzyl, alkylcarbonyl, arylcarbonyl or alkoxycarbonyl groups (R).

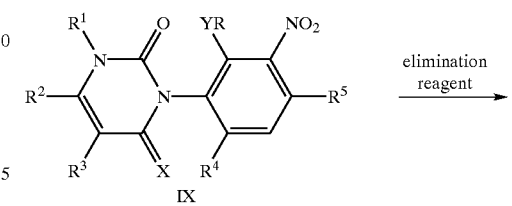

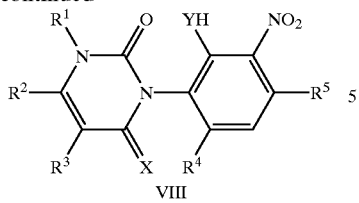

VIII

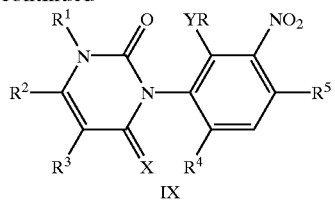

IX

Suitable elimination reagents are, in particular:

for unsubstituted or substituted alkylphenols: trimethylsilyl iodide, boron tribromide, boron trichloride, aluminum trichloride, lithium chloride or hydrogen bromide;

for unsubstituted or substituted benzylphenols or thiophenols: boron trifluoride, hydrofluoric acid or hydrogen/catalyst, preferably noble metal catalysts such as palladium or platinum;

for unsubstituted or substituted aryl esters or aryl thioesters: sodium bicarbonate, sodium carbonate, potassium carbonate, sodium hydroxide, potassium hydroxide, sodium methoxide, hydrogen chloride, sulfuric acid, ammonia, hydrazine or zinc.

The solvent/diluent is preferably chosen so that it is inert to the elimination reagent in question. When using the halides trimethylsilyl iodide, boron tribromide, boron trichloride or aluminum trichloride, halogenated solvents, such as dichloromethane, chloroform, carbon tetrachloride and dichloroethane, are particularly preferred. Hydrogen bromide is preferably used in aqueous solution, very particularly preferably as a 48% strength by weight solution; lithium chloride is preferably employed in polar solvents, such as lower alcohols, dimethyl sulfoxide and dimethylformamide; hydrogenolytic methods are preferably carried out in lower alcohols or carboxylic acids, if appropriate with addition of a hydrogen transfer agent, such as cyclohexene and cyclohexadiene. Mineral bases or mineral acids and nitrogen bases are preferably employed in an aqueous medium. epending on the solubility of the reagents, an organic solvent, for example a lower alcohol, is added if appropriate.

The temperature for the elimination reaction is preferably from 0° C. to the boiling point of the reaction mixture in question.

The elimination reagent is preferably employed in approximately stoichiometric amounts or in an excess. The excess is particularly preferably between one and ten molar equivalents, based on the amount of IX.

Process B)

Nucleophilic exchange of fluorine in nitroaromatics VI by an oxygen or sulfur function.

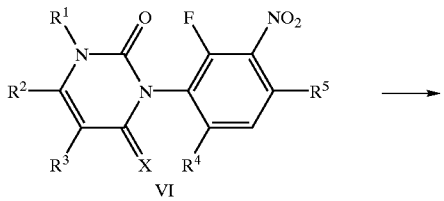

VI

The exchange reaction of aromatically bound fluorine by oxygen or sulfur nucleophiles is carried out in a manner known per se (cf., for example, Houben-Weyl, Methoden der organischen Chemie, Georg Thieme Verlag, Stuttgart, 1976, Vol. 6/1c pp. 146–202 and Volume IX, 4th edition 1955, pp. 7–18).

The following reagents are preferred reaction partners for this reaction:

to exchange F for OR: potassium benzoate, sodium nitrite, sodium hydroxide, potassium hydroxide, potassium carbonate, benzaldoxime, sodium acetate, potassium acetate, sodium methoxide, potassium methoxide, sodium trimethylsilanolate, dimethyl malate.

to exchange F for SR: sodium sulfide, sodium hydrogen sulfide, potassium hydrogen sulfide, benzyl mercaptan.

In certain cases, the reactions can be carried out without solvent/diluent. If a solvent/diluent is employed, preference is given to using those in which the oxygen or sulfur transfer reagent dissolves well. Particular preference is given to alcohols, such as ethanol, propanol or tert-butanol, to aprotic polar solvents, such as dimethylformamide or dimethylacetamide, to cyclic ethers, such as dioxane or tetrahydrofuran, or to aliphatic ethers, such as dimethoxyethane.

The reaction temperatures are preferably at from 20° C. to the reflux temperature of the reaction mixture in question, in particular at from 60° C. to the reflux temperature. The oxygen or sulfur transfer reagent is employed either in an approximately stoichiometric amount or in excess. In suitable cases, it is also possible to employ a very large excess. Preference is given to approximately stoichiometric amounts or to an excess of up to 10 molar equivalents, based on the amount of VI.

The novel nitrophenyluracils VI can be obtained in a manner known per se by nitrating the phenyluracils V (cf., for example, Houben-Weyl, Methoden der organischen Chemie, Georg Thieme Verlag Stuttgart, Vol. 10/1, 1971, p. 479 ff.):

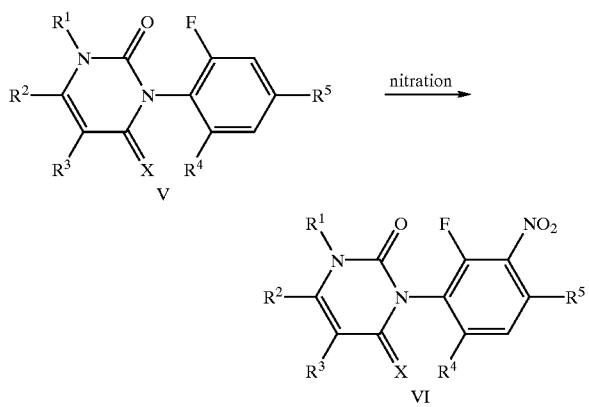

Suitable nitration reagents are, in particular, nitric acid, as a mixture with sulfuric acid or acetic anhydride, or nitronium salts, specifically nitronium tetrafluoroborate. The mixture of nitric acid and sulfuric acid can be composed of any desired proportions of the two components; preference is given to those mixtures where the sulfuric acid greatly predominates or acts as the solvent. Similar comments apply to the mixture of nitric acid and acetic anhydride. Nitronium tetrafluoroborate is preferably employed in aprotic polar solvents, for example in acetonitrile or nitromethane.

The reaction temperature is generally from (−80) to 80° C., in particular from (−20)° C. to 30° C.

When using the reagent nitric acid in the nitration reactions, the process is preferably carried out with an approximately equimolar amount or, particularly preferably, with an excess of nitration reagent. The excess can be many times the amount of V. Nitronium tetrafluoroborate is preferably employed in equimolar amounts relative to V, or in a small excess of between 1.1 and 1.5 molar equivalents.

The phenyluracils V are novel. They can be prepared in a manner known per se from arylureas of the formula III

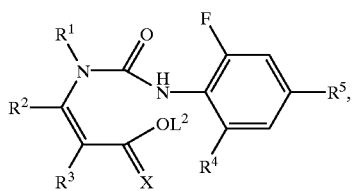

III or from arylanilides of the formula IV

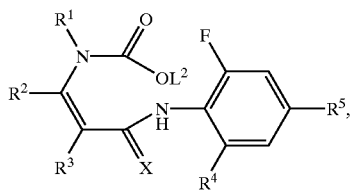

IV ($L^2$ = leaving group, for example $C_1$–$C_4$-alkyl or phenyl). Corresponding processes are disclosed, for example, in WO 97/02253. This application also describes processes according to which the arylureas III or the arylanilides IV can be prepared in a similar manner. For further details, reference is here made to this application. The arylureas III and the arylanilides IV are novel and form part of the subject matter of the present invention.

Process C):

Reaction of a 3-phenylpyrimidinedione derivative I where $R^1$ is hydrogen with an alkylating compound II in a manner known per se:

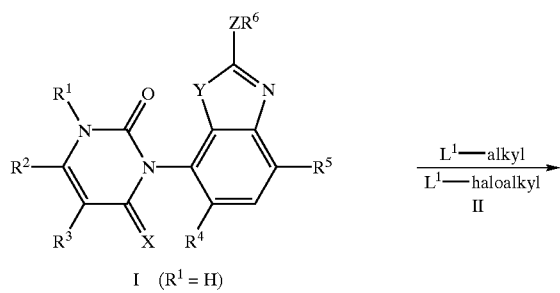

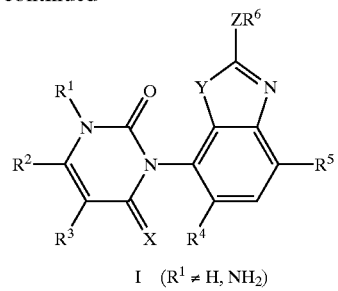

I ($R^1 \neq H, NH_2$)

$L^1$ is a customary leaving group, such as halogen, preferably chlorine, bromine or iodine, (halo)alkylsulfonyloxy, preferably methylsulfonyloxy or trifluoromethylsulfonyloxy, arylsulfonyloxy, preferably toluenesulfonyloxy, and alkoxysulfonyloxy, preferably methoxysulfonyloxy or ethoxysulfonyloxy.

The process is usually carried out in an inert organic solvent, for example in a protic solvent, such as the lower alcohols, preferably in methanol or ethanol, if desired as a mixture with water, or in an aprotic solvent, for example in an aliphatic or cyclic ether, such as methyl tert-butyl ether, 1,2-dimethoxyethane, tetrahydrofuran and dioxane, in an aliphatic ketone, such as acetone, diethyl ketone and ethyl methyl ketone, in an amide, such as dimethylformamide and N-methylpyrrolidone, in a sulfoxide, such as dimethyl sulfoxide, in a urea, such as tetramethylurea and 1,3-dimethyltetrahydro-2(1H)-pyrimidinone, in a carboxylic ester, such as ethyl acetate, or in a halogenated aliphatic or aromatic hydrocarbon, such as dichloromethane, dichloroethane, chlorobenzene and the dichlorobenzenes.

If desired, the process can be carried out in the presence of a base, suitable bases being both inorganic bases, for example carbonates, such as sodium carbonate and potassium carbonate, bicarbonates, such as sodium bicarbonate and potassium bicarbonate, and alkali metal hydrides, such as sodium hydride and potassium hydride, and organic bases, for example amines, such as triethylamine, pyridine and N,N-diethylaniline, or alkali metal alkoxides, such as sodium methoxide, sodium ethoxide and potassium tert-butoxide.

The amount of base and alkylating agent II is preferably in each case 0.5 times to twice the molar amount, based on the amount of starting material I (where $R^1$=hydrogen).

In general, the reaction temperature is from 0° C. to the boiling point of the reaction mixture, in particular from 0 to 60° C.

It is particularly advantageous to prepare the sodium salt by dissolving the phenylpyrimidinedione derivative I where $R^1$=hydrogen in an aqueous sodium hydroxide solution at from 20 to 25° C., using approximately equivalent amounts of phenylpyrimidinedione derivative I (where $R^1$=H) and sodium hydroxide. The corresponding salt of the phenylpyrimidinedione derivative I can then be isolated, for example, by precipitation using a suitable inert solvent, or by evaporation of the solvent.

Salts of phenylpyrimidinedione derivatives I whose metal ion is other than an alkali metal ion can usually be prepared by double decomposition of the corresponding alkali metal salt in aqueous solution, and ammonium, phosphonium, sulfonium and sulfoxonium salts by means of ammonia and phosphonium, sulfonium or sulfoxonium hydroxides.

Process D)

Reaction of a phenylpyrimidinedione derivative of the formula I where $R^1$ is hydrogen with an electrophilic aminating reagent in the presence of a base:

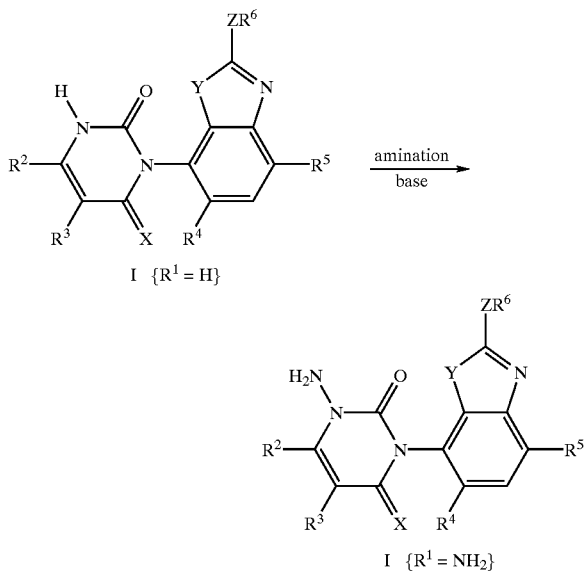

I {$R^1$ = H}

I {$R^1$ = $NH_2$}

An aminating reagent which has hitherto proved itself particularly well is 2,4-dinitrophenoxyamine, but it is also possible to use, for example, hydroxylamine-O-sulfonic acid (HOSA), which is already known from the literature as an aminating reagent (cf., for example, E. Hofer et al., Synthesis 1983, 466; W. Friedrichsen et al., Heterocycles 20 (1983) 1271; H. Hart et al., Tetrahedron Lett. 25 (1984) 2073; B. Vercek et al., Monatsh. Chem. 114 (1983) 789; G. Sosnousky et al., Z. Naturforsch. 38 (1983) 884; R.S. Atkinson et al., J. Chem. Soc. Perkin Trans. 1987, 2787).

The amination can be carried out in a manner known per se (see, for example, T. Sheradsky, Tetrahedron Lett. 1968, 1909; M. P. Wentland et al., J. Med. Chem. 27 (1984), 1103 and, in particular, EP-A 240 194, EP-A 476 697 and EP-A 517 181, which disclose the amination of uracils).

The reaction is normally carried out in a polar solvent, for example in dimethylformamide, N-methylpyrrolidone, dimethyl sulfoxide or in ethyl acetate, which has hitherto proved to be particularly suitable.

Suitable bases are, for example, alkali metal carbonates, such as potassium carbonate, alkali metal alkoxides, such as sodium methoxide and potassium tert-butoxide, or alkali metal hydrides, such as sodium hydride.

The amount of base and aminating reagent is preferably in each case 0.5 times to twice the molar amount, based on the amount of starting material.

Process E)

Sulfurization of a 3-(benzazol-7-yl)pyrimidinedione derivative of the formula I where X is oxygen:

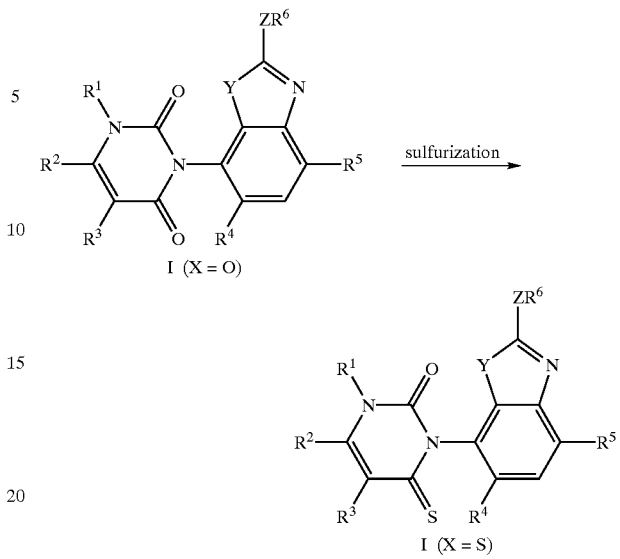

I (X = O)

I (X = S)

In general, sulfurization is effected in an inert solvent or diluent, for example in an aromatic hydrocarbon, such as toluene and the xylenes, in an ether, such as diethyl ether, 1,2-dimethoxyethane and tetrahydrofuran, or in an organic amine, such as pyridine.

Particularly suitable sulfurizing reagents are phosphorus (V) sulfide and 2,4-bis(4-methoxyphenyl)-1,3,2,4-dithiadiphosphetan-2,4-dithione ("Lawesson's reagent").

Usually, once to 5 times the molar amount, based on the starting material to be sulfurized, will suffice for a substantially complete conversion.

The reaction temperature is normally from 20 to 200° C., preferably from 40° C. to the boiling point of the reaction mixture.

Unless otherwise specified, all the processes described above are expediently carried out under atmospheric pressure or under the autogenous pressure of the reaction mixture in question. In general, the reactants are employed in a molar ratio of 0.95:1 to 5:1.

In general, the reaction mixtures are worked up by methods known per se, for example by diluting the reaction solution with water and subsequently isolating the product by means of filtration, crystallization or solvent extraction, or by removing the solvent, partitioning the residue in a mixture of water and a suitable organic solvent and working up the organic phase to give the product.

The compounds I and their agriculturally useful salts are suitable for use as herbicides, both in the form of isomer mixtures and in the form of the pure isomers. The herbicidal compositions which comprise I effect very good control of vegetation on non-crop areas, especially at high rates of application. In crops such as wheat, rice, maize, soya and cotton, they act against broad-leaved weeds and grass weeds without inflicting substantial damage on the crop plants. This effect is observed mainly at low rates of application.

Depending on the application method in question, the compounds, or herbicidal compositions comprising them, can also be employed in a further number of crop plants for eliminating undesirable plants. Examples of suitable crops are the following: *Allium cepa, Ananas comosus, Arachis hypogaea, Asparagus officinalis*, Beta vulgaris spec. altissima, Beta vulgaris spec. rapa, Brassica napus var. napus, Brassica napus var. napobrassica, Brassica rapa var. silvestris, *Camellia sinensis, Carthamus tinctorius, Carya*

*illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

In addition, the compounds I can also be used in crops which, by means of breeding, including genetic engineering methods, have been made tolerant to the action of herbicides.

The compositions or the active ingredients may be applied pre- or post-emergence. If the active ingredients are less well tolerated by certain crop plants, application techniques may be used in which the herbicidal compositions are sprayed, with the aid of the spraying equipment, in such a way that they come in as little contact as possible, if any, with the leaves of the sensitive crop plants while the active ingredients reach the leaves of undesirable plants which grow underneath, or the bare soil surface (post-directed, lay-by).

The compounds I, or the herbicidal compositions comprising them, can be used, for example, in the form of directly sprayable aqueous solutions, powders, suspensions, including highly concentrated aqueous, oily or other suspensions or dispersions, emulsions, oil dispersions, pastes, dusts, materials for spreading or granules, by means of spraying, atomizing, dusting, scattering or watering. The use forms depend on the intended purposes; in any case, they should ensure the finest possible distribution of the active ingredients according to the invention.

Suitable inert auxiliaries are essentially: mineral oil fractions of medium to high boiling point, such as kerosine and diesel oil, furthermore coal tar oils and oils of vegetable or animal origin, aliphatic, cyclic and aromatic hydrocarbons, for example paraffins, tetrahydronaphthalene, alkylated naphthalenes and their derivatives, alkylated benzenes and their derivatives, alcohols, such as methanol, ethanol, propanol, butanol and cyclohexanol, ketones, such as cyclohexanone, or strongly polar solvents, for example amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the 3-(benzazol-7-yl)pyrimidinedione derivatives, as such or dissolved in an oil or solvent, can be homogenized in water by means of wetting agent, tackifier, dispersant or emulsifier. Alternatively, it is possible to prepare concentrates composed of active substance, wetting agent, tackifier, dispersant or emulsifier and, if appropriate, solvent or oil, and these concentrates are suitable for dilution with water.

Suitable surfactants are the alkali metal salts, alkaline earth metal salts and ammonium salts of aromatic sulfonic acids, e.g., ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ethers, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for scattering and dusts can be prepared by mixing or grinding the active substances together with a solid carrier.

Granules, for example coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The concentrations of the active ingredients I in the ready-to-use preparations can be varied within wide ranges. In general, the formulations comprise from 0.001 to 98% by weight, preferably from 0.01 to 95% by weight, of at least one active ingredient. The active ingredients are employed in a purity of from 90% to 100%, preferably 95% to 100% (in accordance with NMR spectra).

The compounds I according to the invention can be formulated, for example, as follows:

I 20 parts by weight of a compound I are dissolved in a mixture 35 composed of 80 parts by weight of alkylated benzene, 10 parts by weight of the adduct of 8 to 10 mol of ethylene oxide and I mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II 20 parts by weight of a compound I are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III 20 parts by weight of an active ingredient I are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV 20 parts by weight of an active ingredient I are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V 3 parts by weight of an active ingredient I are mixed with 97 parts by weight of finely divided kaolin. This gives a dust which comprises 3% by weight of the active ingredient.

VI 20 parts by weight of an active ingredient I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of a compound I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of a compound I is dissolved in a mixture composed of 80 parts by weight of cyclohexanone and 20 parts by weight of Wettol® EM 31 (nonionic emulsifier based on ethoxylated castor oil). This gives a stable emulsion concentrate.

To widen the spectrum of action and to achieve synergistic effects, the [benz(ox/othi)azol-7-yl]-1H-pyrimidine-2,4-diones according to the invention may be mixed with a large number of representatives of other groups of herbicidal or growth-regulating active ingredients and applied jointly. Suitable components for mixtures are, for example, 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, bipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Furthermore, it may be advantageous to apply the compounds I, alone or in combination with other herbicides, also as a mixture with other crop protection agents, for example with pesticides or agents for controlling phytopathogenic fungi or bacteria. Also of interest is the miscibility with mineral salt solutions which are employed for remedying nutritional and trace-element deficiencies. Nonphytotoxic oils and oil concentrates may also be added.

Depending on the control target, the season, the target plants and the growth stage, the rates of application of active ingredient I are from 0.001 to 3.0, preferably 0.01 to 1.0, kg/ha active substance (a.s.).

PREPARATION EXAMPLES

Example 1

3-[4-Chloro-2-cyclopentyl-6-fluorobenzoxazol-7-yl]-1-methyl-6-trifluoromethyl-2,4-(1H,3H)-pyrimidinedione (Comp. Ia.3 from Table 1)

0.48 g of 3-[3-amino-4-chloro-6-fluoro-2-hydroxyphenyl]-1-methyl-6-trifluoromethyl-2,4-(1H,3H)-pyrimidinedione (from intermediate 7) was initially charged with 0.14 g of triethylamine in 30 ml of absolute xylene, and the mixture was, at 0° C., admixed dropwise with 0.18 g of cyclopentanecarbonyl chloride. After 10 minutes, the mixture was warmed to 20° C., 0.1 g of pyridinium p-toluenesulfonate was added and the mixture was heated at reflux for six hours. After cooling, the xylene phase was washed three times with 30 ml of water each time, dried over sodium sulfate and freed from the solvent under reduced pressure. The crude product was purified by medium pressure liquid chromatography (MPLC); mobile phase: cyclohexane/ethyl acetate (9:1). Yield: 0.27 g;

1H-NMR (200 MHz, in $CDCl_3$): δ [ppm]=7.25 (d, 1H), 6.40 (s, 1H), 3.60 (s, 3H), 3.30 (quin, 1H), 1.50–2.25 (m, 8H).

Intermediate 1

4-Chloro-2,6-difluoroaniline 35.5 g of 2,6-difluoroaniline were mixed with 200 ml of concentrated acetic acid, and the mixture was heated to 80° C. 42.4 g of sulfuryl chloride were mixed with approximately the same amount of concentrated acetic acid, and the mixture was added dropwise to the heated solution. The mixture was then heated at reflux for six hours. After cooling, the solution was concentrated under reduced pressure and the residue was stirred with water and pentane. The solid residue was filtered off and washed with water. The resulting solid was admixed with 200 ml of concentrated hydrochloric acid and heated at reflux for two hours. After cooling, the solution was carefully made slightly alkaline using aqueous sodium hydroxide solution, and the mixture was extracted three times with 100 ml of ethyl acetate each time. The organic phase was dried over sodium sulfate and freed from the solvent. Yield: 40 g;

1H-NMR (270 MHz, in $CDCl_3$): δ [ppm]=6.85 (d, 2H), 3.5–3.9 (br, 2H).

Intermediate 2

4-Chloro-2,6-difluorophenyl Isocyanate 40 g of 4-chloro-2,6-difluoroaniline were dissolved in 300 ml of absolute toluene. With stirring, 100 ml of trichloromethyl chloroformate were added dropwise at 20° C. The mixture was slowly heated to reflux. After three and half hours, the mixture was concentrated and the resulting isocyanate was used directly for the synthesis of intermediate 3.

Intermediate 3

3-[4-Chloro-2,6-difluorophenyl]-6-trifluoromethyl-2,4-(1H,3H)-pyrimidinedione 7.2 g of sodium hydride were initially charged in 300 ml of absolute dimethylformamide and, at 0° C., 44 g of ethyl 3-amino-4,4,4-trifluorobut-2-enoate (dissolved in a little dimethylformamide) were added dropwise. The mixture was stirred at this temperature for two hours. The mixture was cooled to (−20)° C. and the isocyanate (intermediate 2) was added dropwise in a little absolute tetrahydrofuran. After the addition had ended, the mixture was warmed to 20° C. and stirred for 18 hours. The volatile components were then removed under reduced pressure, and the mixture was then admixed with dilute hydrochloric acid and extracted with methyl tert-butyl ether (three times 100 ml). The organic phase was dried over sodium sulfate and freed from the solvent. Yield: 72.0 g; 1H-NMR (270 MHz, CDCl$_3$): δ [ppm]=7.10 (d, 2H), 6.25 (s, 1H).

Intermediate 4

3-[4-Chloro-2,6-difluorophenyl]-1-methyl-6-trifluoromethyl-2,4-(1H,3H)-pyrimidinedione 71 g of 3-[4-chloro-2,6-difluorophenyl]-6-trifluoromethyl-2,4-35 (1H,3H)-pyrimidinedione were initially charged in 200 ml of absolute dimethylformamide and, at 20° C., 29.0 g of potassium carbonate and then, dropwise, 29.8 g of methyl iodide were added. The mixture was stirred for 18 hours. The solvent was removed under reduced pressure, the residue was admixed with water and the mixture was extracted with methyl tert-butyl ether. The extract was dried over sodium sulfate and the solvent was then removed under reduced pressure. Yield: 58.0 g;

1H-NMR (270 MHz, in CDCl$_3$): δ [ppm]=7.10 (d, 2H), 6.40 (s, 1H), 3.55 (s, 3H).

Intermediate 5

3-[4-Chloro-2,6-difluoro-3-nitrophenyl]-1-methyl-6-trifluoromethyl-2,4-(1H,3H)-pyrimidinedione 58 g of 3-[4-chloro-2,6-difluorophenyl]-1-methyl-6-trifluoromethyl-2,4-(1H,3H)-pyrimidinedione were dissolved in 400 ml of concentrated sulfuric acid and, at 0° C., admixed dropwise with a mixture of 10.7 g of 98% strength nitric acid and 10 ml of concentrated sulfuric acid. The mixture was stirred at 0° C. for 30 minutes and then at 20° C. for 18 hours. Another 10.7 g of the acid mixture were then added dropwise at 0° C. The mixture was stirred at 20° C. for two hours and then poured into ice-water, and the resulting precipitate was filtered off with suction and washed with water until neutral. The solid was dried in a vacuum drying cabinet. Yield: 58.0 g;

1H-NMR (270 MHz, in CDCl$_3$): δ [ppm]=7.30 (d, 1H), 6.40 (s, 1H), 3.60 (s, 3H).

Intermediate 6

3-[4-Chloro-6-fluoro-2-hydroxy-3-nitrophenyl]-1-methyl-6-trifluoromethyl-2,4-(1H,3H)-pyrimidinedione 30 g of 3-[4-chloro-2,6-difluoro-3-nitrophenyl]-1-methyl-6-trifluoromethyl-2,4-(1H,3H)-pyrimidinedione were dissolved in 100 ml of absolute dimethylformamide, admixed with 25.2 g of sodium acetate and heated at 100° C. for four hours. After cooling, the solvent was removed under reduced pressure and the residue was admixed with water; by addition of dilute hydrochloric acid, the pH was taken into the acidic range, and the mixture was extracted with methyl tert-butyl ether (three times 75 ml). The product of value was obtained as a mixture with the isomer formed by exchange of the fluorine atom which is in the position para to the nitro group. Total yield: 28.3 g. The crude product was purified at the subsequent stage (intermediate 7).

1H-NMR (270 MHz, in CDCl$_3$): δ [ppm]=7.05 (d, 1H), 6.40 (s, 1H), 3.55 (s, 3H).

Intermediate 7

3-[3-Amino-4-chloro-6-fluoro-2-hydroxyphenyl]-1-methyl-6-trifluoromethyl-2,4-(1H,3H)-pyrimidinedione 28 g of the crude product (intermediate 6) were dissolved in a mixture of 260 ml of water, 50 ml of ethanol and 26.7 ml of concentrated hydrochloric acid. The mixture was heated to 65° C., and 20.7 g of iron powder were added a little at a time. The mixture was refluxed for six hours. After cooling, the mixture was extracted with ethyl acetate (300 ml). The crude product obtained by removing the solvent under reduced pressure was purified by column chromatography (mobile phase: cyclohexane/ethyl acetate=8:2). Yield: 2.8 g;

1H-NMR (270 MHz, in CDCl$_3$): δ [ppm]=6.80 (d, 1H), 6.30 (s, 1H), 4.6–5.2 (br, 2H), 3.50 (s, 3H).

In addition to the compounds described above, other 3-[benz(ox/othi)azol-7-yl]-1H-pyrimidine-2,4-diones of the formula I which were, or can be, prepared in a similar manner are listed in Table 5 below:

TABLE 2

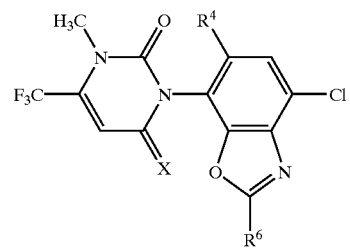

{Z = chemical bond; R$^1$ = CH$_3$; R$^2$ = CF$_3$; R$^3$ = H; R$^5$ = Cl}

| Ex. No. | X | R$^4$ | R$^6$ | m.p. [° C.] |
|---|---|---|---|---|
| 1 | O | F | cyclopentyl | oil |
| 2 | O | F | cyclohexyl | oil |
| 3 | O | F | tetrahydropyran-3-yl | oil |
| 4 | O | F | H | 185 |
| 5 | O | F | cyclopropyl | oil |
| 6 | O | F | tetrahydropyran-4-yl | oil |
| 7 | O | F | tetrahydrothiopyran-4-yl | oil |
| 8 | O | F | cyclobutyl | oil |
| 9 | S | F | cyclobutyl | oil |
| 10 | O | H | cyclopentyl | oil |
| 11 | O | H | cyclopropyl | oil |

The herbicidal activity of the 3-[benz(ox/othi)azol-7-yl]-1H-pyrimidine-2,4-diones of the formula I was demonstrated by greenhouse experiments:

The growing containers used were plastic pots containing loamy sand with approximately 3.0% of humus as the substrate. The seeds of the test plants were sown separately for each species.

In the pre-emergence treatment, the active ingredients which had been suspended or emulsified in water were applied immediately after sowing by means of finely distributing nozzles. The containers were irrigated gently to promote germination and growth and subsequently covered with translucent plastic hoods until the plants had rooted. This cover causes uniform germination of the test plants, unless this has been adversely affected by the active ingredients.

For the post-emergence treatment, the test plants were first grown to a plant height of 3 to 15 cm, depending on the growth habit, and only then treated with the active ingredients which had been suspended or emulsified in water. The test plants were either sown directly and grown in the same containers or first grown separately as seedlings and transplanted into the test containers a few days prior to treatment. The rate of application for the post-emergence treatment was only 15.6 or 7.8 kg/ha of a.s. (active substance).

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants or complete destruction of at least the aerial parts, and 0 means no damage or normal course of growth.

The plants used in the greenhouse experiments belonged to the following species:

| Scientific name | Common name |
| --- | --- |
| Abutilon theophrasti | velvet leaf |
| Amaranthus retroflexus | redroot pigweed |
| Chenopodium album | lambsquarters |
| Solanum nigrum | black nightshade |

At application rates of only 15.6 or 7.8 kg/ha, compound No.Ia.3 effected complete destruction of the 4 test plants listed above (efficacy 100%).

We claim:

1. A compound of formula I

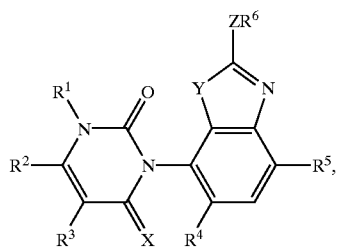

in which:
- X is oxygen or sulfur;
- Y is oxygen or sulfur;
- Z is a chemical bond, $C_1$–$C_4$-alkylene, oxygen, sulfur, SO or $SO_2$;
- $R^1$ is hydrogen, amino, $C_1$–$C_6$-alkyl or $C_1$–$C_6$-haloalkyl;
- $R^2$ is hydrogen, halogen, $C_1$–$C_6$-alkyl, $C_1$–$C_6$-haloalkyl, $C_1$–$C_6$-alkylthio, $C_1$–$C_6$-alkylsulfinyl or $C_1$–$C_6$-alkylsulfonyl;
- $R^3$ is hydrogen, halogen or $C_1$–$C_6$-alkyl;
- $R^4$ is hydrogen or halogen;
- $R^5$ is cyano, halogen, $C_1$–$C_6$-alkyl, $C_1$–$C_6$-haloalkyl, $C_1$–$C_6$-alkoxy or $C_1$–$C_6$-haloalkoxy;
- $R^6$ is hydrogen, $C_3$–$C_7$-cycloalkyl or 3- to 7-membered saturated heterocyclyl containing one or more oxygen and/or sulfur atoms, where each cycloalkyl and each heterocyclyl ring may contain a carbonyl or thiocarbonyl ring member,
  and where each cycloalkyl and heterocyclyl ring may be unsubstituted or may carry from one to four substituents, in each case selected from the group consisting of cyano, nitro, amino, hydroxyl, halogen, $C_1$–$C_4$-alkyl, $C_1$–$C_4$-haloalkyl, $C_1$–$C_4$-cyanoalkyl, $C_1$–$C_4$-hydroxyalkyl, $C_1$–$C_4$-aminoalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy, di($C_1$–$C_4$-alkyl)amino, $C_3$–$C_6$-alkenyl, $C_3$–$C_6$-alkynyl, $C_3$–$C_4$-alkenyloxy, $C_3$–$C_4$-alkenylthio, $C_3$–$C_4$-alkynyloxy and $C_3$–$C_4$-alkynylthio,
  with the proviso that $R^6$ is hydrogen only if Y is oxygen and Z is a chemical bond and that $R^6$ is not $C_3$–$C_6$-cycloalkyl if Y is sulfur, or an agriculturally useful salt of a compound of formula I.

2. The compound of formula I defined in claim 1 where
- X is oxygen,
- Z is a chemical bond, $C_1$–$C_4$-alkylene, oxygen or sulfur,
- $R^1$ is hydrogen, amino or $C_1$–$C_6$-alkyl,
- $R^2$ is hydrogen, halogen, $C_1$–$C_6$-alkyl, $C_1$–$C_6$-haloalkyl or $C_1$–$C_6$-alkylsulfonyl,
- $R^3$ is hydrogen,
- $R^4$ is hydrogen, fluorine or chlorine and
- $R^5$ is cyano or halogen.

3. The compound of formula I defined in claim 1 or its agriculturally useful salt, wherein
- X is oxygen;
- Y is oxygen;
- Z is a chemical bond or $C_1$–$C_4$-alkylene;
- $R^1$ is hydrogen, amino or $C_1$–$C_6$-alkyl;
- $R^2$ is trifluoromethyl;
- $R^3$ is hydrogen;
- $R^4$ is hydrogen, fluorine or chlorine;
- $R^5$ is cyano or halogen; and
- $R^6$ is hydrogen, $C_3$–$C_7$-cycloalkyl or a 3- to 7-membered saturated heterocycle containing one oxygen atom, where each cycloalkyl and each heterocyclyl ring optionally contains a carbonyl or thiocarbonyl ring member.

4. The compound of formula I defined in claim 1 or its agriculturally useful salt, wherein
- X is oxygen;
- Y is oxygen;
- Z is a chemical bond or $C_1$–$C_4$-alkylene;
- $R^1$ is methyl;
- $R^2$ is trifluoromethyl;
- $R^3$ is hydrogen;
- $R^4$ is hydrogen, fluorine or chlorine;
- $R^5$ is cyano or halogen; and
- $R^6$ is hydrogen or $C_3$–$C_7$-cycloalkyl.

5. The compound of formula I defined in claim 1 or its agriculturally useful salt, wherein
- X is oxygen;
- Y is oxygen;
- Z is a chemical bond or methylene;
- $R^1$ is methyl;
- $R^2$ is trifluoromethyl;

R³ is hydrogen;

R⁴ is hydrogen, fluorine or chlorine;

R⁵ is cyano or halogen; and

R⁶ is hydrogen or $C_3$–$C_7$-cycloalkyl.

6. The compound of formula I defined in claim 1 or its agriculturally useful salt, wherein X is oxygen;

Y is oxygen;

Z is a chemical bond or methylene;

R¹ is methyl;

R² is trifluoromethyl;

R³ is hydrogen;

R⁴ is fluorine;

R⁵ is halogen; and

R⁶ is hydrogen or $C_3$–$C_7$-cycloalkyl.

7. A process for preparing the compound of formula I defined in claim 1, which comprises condensing an aminophenol or an aminothiophenol of formula VII

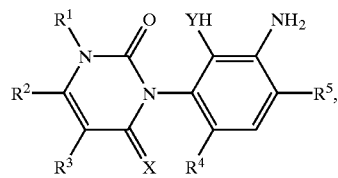

with a carboxylic acid derivative or a carbonic acid derivative.

8. A herbicidal composition, comprising a herbicidally effective amount of at least one compound of formula I as defined in claim 1 or an agriculturally useful salt thereof, and at least one liquid or solid carrier and optionally at least one surfactant.

9. A process for preparing the herbicidal composition defined in claim 8, which comprises mixing a herbicidally effective amount of at least one compound of formula I or an agriculturally useful salt thereof with at least one inert liquid or solid carrier and optionally at least one surfactant.

10. A method for controlling undesirable vegetation, which comprises allowing a herbicidally effective amount of at least one compound of formula I as defined in claim 1, or of an agriculturally useful salt thereof, to act on plants, their habitat or on seeds.

* * * * *